United States Patent [19]

Jacklich

[11] Patent Number: 4,911,639

[45] Date of Patent: Mar. 27, 1990

[54] HANDPIECE FOR USE IN ROOT CANAL PROCEDURES

[76] Inventor: John J. Jacklich, 102 Western Ct., Santa Cruz, Calif. 95060

[21] Appl. No.: 800,207

[22] Filed: Nov. 21, 1985

[51] Int. Cl.[4] .............................................. A61C 5/02
[52] U.S. Cl. .................................. 433/102; 433/119; 433/127
[58] Field of Search ............... 433/127, 128, 102, 118, 433/119, 224, 147

[56] References Cited

U.S. PATENT DOCUMENTS

| | | | |
|---|---|---|---|
| 797,684 | 8/1905 | Harper | 433/147 |
| 904,990 | 11/1908 | Powers | 433/147 |
| 1,203,083 | 10/1916 | Van Woert | 433/147 |
| 3,924,334 | 12/1975 | Lentine et al. | 433/102 |
| 3,967,380 | 7/1976 | Malata et al. | 433/122 |
| 4,021,917 | 5/1977 | Nakanishi | 433/126 |
| 4,044,468 | 8/1977 | Kahn | 433/102 |
| 4,229,168 | 10/1980 | Scholz | 433/124 |
| 4,243,388 | 1/1981 | Arai | 433/27 |
| 4,260,379 | 4/1981 | Groves et al. | 433/102 |
| 4,268,252 | 5/1981 | Lustig | 433/128 |
| 4,295,827 | 10/1981 | Martin et al. | 433/81 |
| 4,299,571 | 11/1981 | McSpadden | 433/102 |
| 4,332,561 | 6/1982 | McSpadden | 433/102 |
| 4,484,891 | 11/1984 | Nash | 433/116 |
| 4,505,676 | 3/1985 | Gonser | 433/119 |
| 4,536,156 | 8/1985 | Cattin | 433/102 |
| 4,580,979 | 4/1986 | Leonard | 433/127 |
| 4,609,352 | 9/1986 | Riitano | 433/102 |

FOREIGN PATENT DOCUMENTS

207037 1/1960 Fed. Rep. of Germany ...... 433/102

OTHER PUBLICATIONS

Osada Electric Co. "ENAC," undated, No. CN08504-30.
Caulk Endodontics; "Caulk Endoplus," 1985, Brochure.
Medidenta International, Inc.; "Sonic Breakthrough", Brochure.

Primary Examiner—John J. Wilson

[57] ABSTRACT

An improved ultrasonic handpiece adapter for use in root canal procedures is provided in which a fire well is formed in the body of the device. The lower surface of the file well is frusto-conical in shape and receives a file wherein an enlarged file head has a frusto-conical shape at its bottom which seats against the lower surface of the file well when downward pressure is exerted on the file and which floats with respect to the lower surface of the file well when upward pressure is exerted on the file. A clutch mechanism is thereby provided wherein the file blade is in its engaged position during a cutting stroke and wherein the file blade floats during the motion of positioning the blade for the next cutting stroke. A cutting file has the tip of its shank flared so that the shank is prevented from being pulled through the file head. The apparatus may be connected to a conventional source of sub-sonic or ultrasonic power.

6 Claims, 2 Drawing Sheets

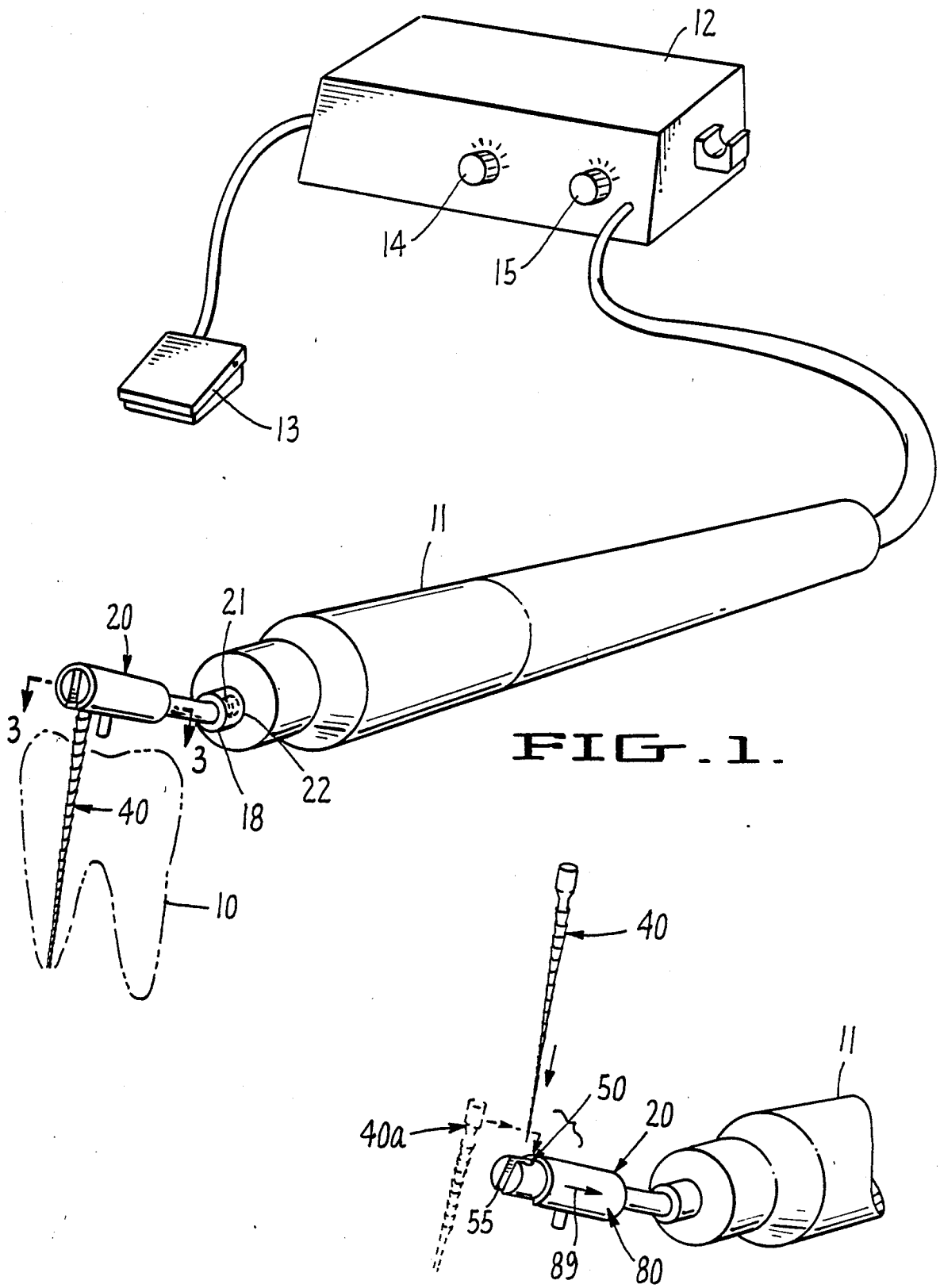

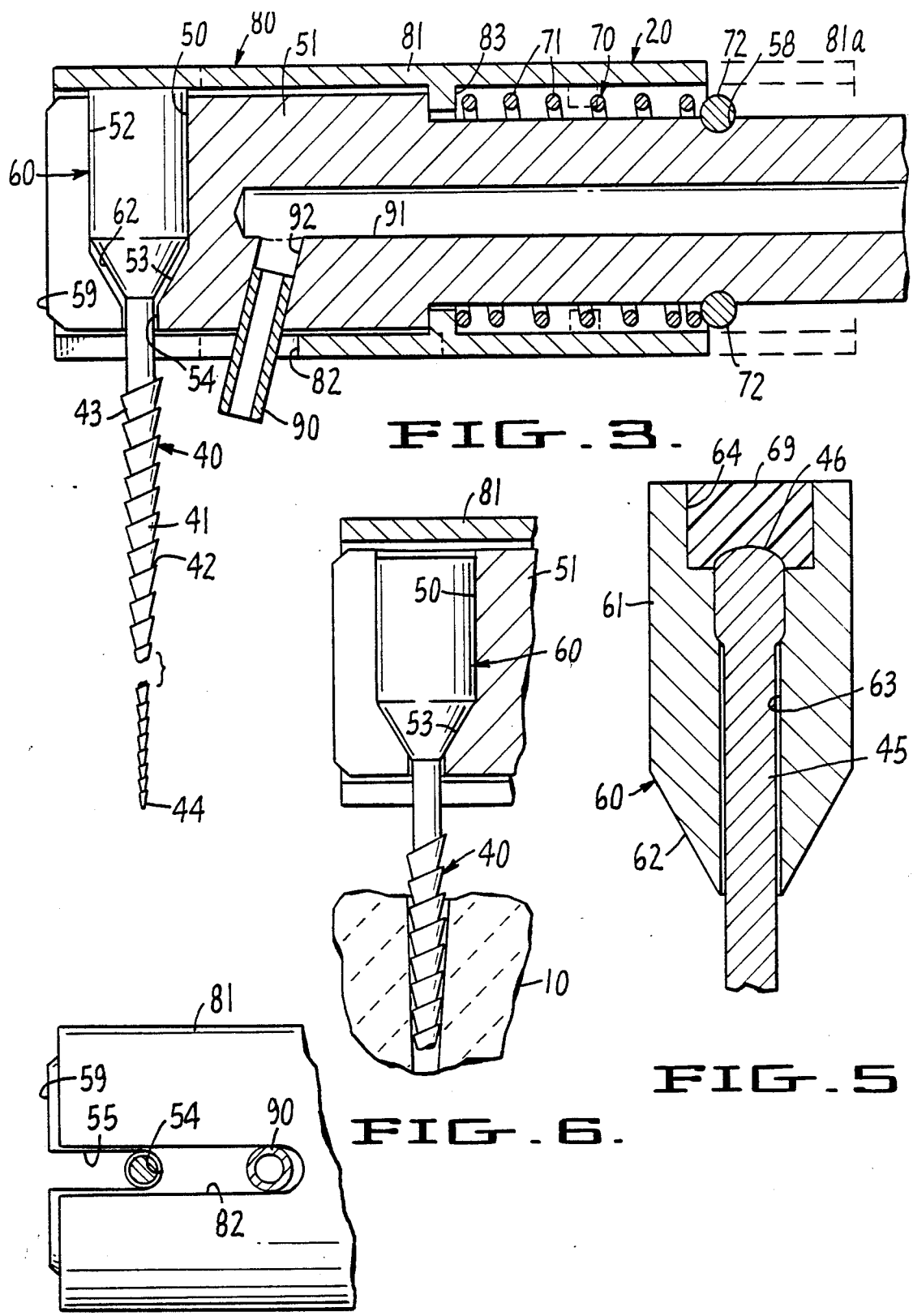

HANDPIECE FOR USE IN ROOT CANAL PROCEDURES

CROSS REFERENCE TO RELATED APPLICATION

The apparatus disclosed herein may be used in conjunction with the file bade disclosed in my application entitled "Endodontic File," submitted simultaneously with this application.

BRIEF SUMMARY OF THE INVENTION

This invention relates generally to ultrasonic handpieces for use in root canal procedures. More particularly, this invention provides an adapter which connects to a conventional sonic powered dental scaler handpiece, wherein the adapter has a clutch mechanism between the file and the body portion of the adapter which carries the file so that during an upward cutting stroke of the blade, the clutch is engaged and the blade is cutting at maximum efficiency. During a downward, non-cutting movement of the handpiece, the clutch is disengaged and the blade of the file is not in a cutting mode.

Accordingly, a primary object of the invention is to provide an adapter for an ultrasonic scaler handpiece for use in root canal procedures in which the file blade is fully engaged in a cutting stroke of the instrument but which is disengaged or free floating during a non-cutting stroke of the instrument.

A further object of the invention is to provide an adapter for an ultrasonic handpiece in which the file blade is firmly anchored in its support mechanism.

A further object of the invention is to provide an endodontic adapter which is readily connected to a conventional ultrasonic or sub-sonic device such as a scaler.

Yet another object of the invention is to provide a sonic/ultrasonic handpiece for root canal procedures wherein a movable safety housing is provided which prevents the file blade from separating from the handpiece during operation but which is movable to allow the ready removal of an old file blade from the instrument or the prompt insertion of a new file blade into the instrument.

A further object is to provide an alternate system for ready insertion of new blades (and ready removal of used blades) through a slot formed in the handpiece adapter.

Other objects and advantages of the invention will become apparent from the following description of a preferred embodiment and the drawings, wherein:

BRIEF DESCRIPTION OF THE DRAWINGS

FIG. 1 is a schematic representation showing the apparatus in use during a root canal procedure;

FIG. 2 is a perspective showing of a file about to be inserted into the body of the apparatus;

FIG. 3 is a section along the line 3—3 of FIG. 1;

FIG. 4 is a bottom view of the apparatus shown in FIG 3;

FIG. 5 is a sectional view of a portion of the device shown in FIG. 3; and

FIG. 6 is a sectional view of a portion of the device during a cutting stroke of the file blade.

DETAILED DESCRIPTION OF THE DRAWINGS

Referring to FIG. 1, a tooth 10 is shown in which a root canal procedure is being carried cut by the adapter shown generally as 20 according to this invention and file means 40 according to this invention. A conventional sonic or ultrasonic scaler handpiece 11 is shown which is not a part of this invention but which is a conventional handpiece. An ultrasonic power source 12 is shown with a control pedal 13 and control knobs 14 and 15 for power and water, and which likewise do not constitute a portion of this invention.

According to this invention, adapter 20 is provided which connects readily to conventional handpiece 11 by internal threads 21 at the end portion 22 of adapter 20 which thread into fitting 18 at the tip of handpiece 11. Threads 21 form connector means to handpiece 11. It is to be understood that the method of connecting the adapter to the scaler may vary depending on the particular scaler. In this fashion, a conventional scaler owned by a dentist can be readily converted to an endodontic device capable of performing root canal procedures by removal of the scaling tip and application of adapter 20 to the scaling handpiece 11.

FIG. 2 shows file means 40 about to be inserted into file well 50 formed in body 51 of adapter 20. The Lop of file well 50 is exposed by moving safety housing means 80 in the direction of arrow 89 by the user to facilitate insertion of file means 40. File means 40 may be inserted into file well 50 either from above as shown at 40; or from the front as shown in phantom at 40a through blade insertion slot 55.

FIG. 3 shows body 51 which is generally an elongated cylinder made of stainless steel. File well 50 is formed in body 51 having an upper cylindrical surface 52 and a lower frusto-conical surface 53. File well 50 is formed near the tip 59 of body 51.

File means 40 comprises a file blade 41 which is an elongated blade with a continuous 22 degree constant helical angle 42 formed thereon. The diameter of file blade 41 decreases from its upper end 43 to its lower end 44. The precise design of the cutting edges of file means 40 is immaterial to the present invention. One design is stated for completeness.

File head 60 is shown best in FIG. 5 and comprises an upper cylindrical portion 61 and a lower frusto-conical surface 62 which is designed to seat against surface 53 of file well 50. A cylindrical passageway 63 is formed in file head 60 to receive the shank 45 of file blade 41. The tip 46 of shank 45 is tapered so that shank 45 cannot fall downwardly through passageway 63 during operation of the device. An upper cylindrical recess 64 is provided in file head 60 which is filled with epoxy cement 69 which further bonds shank 45 to file head 60 and is used for color coding the size of the file blade.

FIG. 3 shows the device in a mode where file means 40 is floating with respect to file well 50. This mode occurs when upward pressure is exerted on file means 40 as for example when the device is being positioned by the user for a cutting stroke. FIG. 6 shows the device during a cutting stroke during which the tapered lower portion of file head 60 is seated against the lower tapered surface 53 of file well 50. In this position, the ultrasonic power delivered to body 51 by power source 12 causes a non-directional, rapid vibration of file means 40 because file head 60 is engaged against the lower, frusto-conical portion 53 of file well 50. During this cutting stroke, the upper surface of the threads perform a cutting stroke with respect to tooth 10. In the mode shown in FIG. 3, even though body 51 is vibrating the vibration is not transmitted to file means 40 and file means 40 may be positioned within tooth 10 to prepare for the next cutting stroke. The seating of file head 60 against file well 50 forms a tapered clutch which is engaged in an upward, cutting stroke and is disengaged during downward movement of the blade.

Safety housing means 80 is provided which moves from a position shown in FIG. 3 to a position shown in phantom by dotted lines 81a. In the position shown in FIG. 3 safety housing means extends over file well 50 to prevent file means 40 from being driven upwardly cut of body 51. Safely housing means 80 comprises a cylindrical sheath 81 which has a notch 82 formed in its lower portion to clear file means 40 and water nozzle 90. Internal spring means 70 comprises a helical spring 71 which seats against flange 83 formed on the inside of cylindrical sheath 81. Helical spring 71 at its other end seats against C-ring 72 which is carried in recess 58 of body 51. Internal spring means 70 holds safety housing 80 in a first position shown in FIG. 3 wherein safety housing 80 covers file well 50. Safety housing 80 may be easily moved by the user to a second position shown by the dotted lines 81a wherein file well 50 is uncovered as shown best in FIG. 2 to facilitate removal of an old file means or insertion of a new file means.

FIG. 4 is a bottom view of the apparatus in which the end 59 of body 51 has a blade insertion slot 55 formed therein extending from the base 54 of file well 50 to the tip or end 59 of body 51. Blade insertion slot 55 facilitates the ready insertion of a new blade into file well 50 and the ready removal of a used blade from file well 50 as shown best in FIG. 2. Blade insertion slot 55 is vertical, extends through body 51 and has a width slightly greater than the diameter of shank 45 to permit insertion of blade means 40 from the front of the apparatus.

Passageway 91 is formed in body 51 to supply water to water nozzle 90 through a communicating passageway 92. This allows a water jet to be directed at the general working area of file means 40 during root canal procedures.

File means 40 as shown in FIGS. 3–6 comprises two pieces, namely the file head 60 and the file blade 41. It is understood that file means 40 may be constructed of a single piece of material having an enlarged file head. The preferred embodiment of file means 40 is a two piece unit as shown in FIG. 5 to minimize manufacturing costs.

What is claimed is:

1. An adapter for use in root canal procedures, comprising:
    a body,
    a file well formed in said body, wherein the lower surface of said file well is frusto-conical in shape,
    file means adapted to be removably carried by said file well, and adapted to be driven by ultrasonic or subsonic power, said file means having a file head with a frusto-conical shape at its bottom, the surface of which seats against the lower surface of said file well such that the seating of said frusto-conical surfaces forms a tapered clutch means which is engaged only when downward pressure is exerted on said file means, and said tapered clutch means disengaging with respect to the lower surface of said file well when upward pressure is exerted on said file means.

2. The apparatus of claim 1 wherein said file means has a cylindrical shank, said file head has an upper cylindrical portion of greater diameter than said shank of said file means, said file head having a cylindrical passageway formed therein for receiving said shank, and wherein the tip of said shank is flared to prevent said shank from falling through said passageway.

3. The apparatus of claim 1 further comprising connector means carried by said body to removably connect said adapter to a conventional ultrasonic power source.

4. The apparatus of claim 1 further comprising safety housing means which extends over at least the file well portion of said body to prevent said file means from being driven upwardly out of said body.

5. The apparatus of claim 4 wherein said safety housing means is spring loaded by an internal spring means such that said safety housing means is held by said internal spring means in a first position covering said file well, but which may be easily moved by the user to a second position uncovering said file well to facilitate removal or insertion of said file means.

6. The apparatus of claim 1 further comprising a blade insertion slot formed at the end of said body to facilitate ready insertion of a new blade and ready removal of a used blade.

* * * * *